(12) United States Patent  
Huang et al.

(10) Patent No.: US 11,493,500 B2  
(45) Date of Patent: Nov. 8, 2022

(54) CATCHER, CAPTURE DEVICE, AND METHOD FOR CAPTURING TARGET BIOLOGICAL PARTICLE

(71) Applicant: CYTOAURORA BIOTECHNOLOGIES, INC., Hsinchu County (TW)

(72) Inventors: Chung-Er Huang, Hsinchu County (TW); Sheng-Wen Chen, Hsinchu County (TW); Hsin-Cheng Ho, Hsinchu County (TW); Hei-Jen Jou, Hsinchu County (TW); Ming Chen, Hsinchu County (TW)

(73) Assignee: CYTOAURORA BIOTECHNOLOGIES, INC., Hslnchu County (TW)

( * ) Notice: Subject to any disclaimer, the term of this patent is extended or adjusted under 35 U.S.C. 154(b) by 465 days.

(21) Appl. No.: 16/826,301

(22) Filed: Mar. 23, 2020

(65) Prior Publication Data

US 2021/0293778 A1 Sep. 23, 2021

(51) Int. Cl.
| | |
|---|---|
| *G01N 33/487* | (2006.01) |
| *G01N 1/10* | (2006.01) |
| *G01N 33/80* | (2006.01) |
| *B01L 3/00* | (2006.01) |
| *G01N 1/40* | (2006.01) |

(52) U.S. Cl.
CPC .. *G01N 33/48778* (2013.01); *B01L 3/502761* (2013.01); *G01N 1/10* (2013.01); *G01N 1/4077* (2013.01); *G01N 33/80* (2013.01); *B01L 2200/0668* (2013.01); *B01L 2400/086* (2013.01)

(58) Field of Classification Search
CPC ......... B01L 2400/086; B01L 3/502761; G01N 1/4077
See application file for complete search history.

(56) References Cited

U.S. PATENT DOCUMENTS

| | | | |
|---|---|---|---|
| 2015/0260710 A1 | 9/2015 | Tseng et al. | |
| 2015/0285808 A1 | 10/2015 | Nagrath et al. | |
| 2017/0299495 A1 | 10/2017 | Huang et al. | |
| 2018/0266951 A1* | 9/2018 | Spero | G01N 21/05 |
| 2019/0001320 A1 | 1/2019 | Huang et al. | |
| 2022/0017846 A1* | 1/2022 | Vulto | B01L 3/50273 |

FOREIGN PATENT DOCUMENTS

TW M550302 U 10/2017

* cited by examiner

*Primary Examiner* — Christopher Adam Hixson  
(74) *Attorney, Agent, or Firm* — Li & Cai Intellectual Property Office

(57) ABSTRACT

A catcher, a capture device, and a method for capturing at least one target biological particle are provided. The catcher includes a base and a plurality of capture arms extending from the base and spaced apart from each other. Each of the capture arms has a free end portion configured to capture a target biological particle and a supporting segment connected between the free end portion and the base. The supporting segment of each of the capture arms is arranged in a projection space defined by orthogonally projecting the free end portion along a height direction onto the base. When the target biological particle is captured by two of the capture arms that are bent and arranged adjacent to each other, a part of the target biological particle is trapped by the supporting segments of the two of the capture arms and is held.

20 Claims, 13 Drawing Sheets

CATCHER, CAPTURE DEVICE, AND METHOD FOR CAPTURING TARGET BIOLOGICAL PARTICLE

FIELD OF THE DISCLOSURE

The present disclosure relates to a catcher, and more particularly to a catcher, a capture device, and a method for capturing at least one target biological particle.

BACKGROUND OF THE DISCLOSURE

In recent years, non-invasive capture of rare cells using non-invasive detection has been applied to different types of auxiliary diagnosis, such as prenatal detection or tracking and metastatic diagnosis of early cancer course.

Specifically, circulating tumor cells (CTC) are tumor cells that are separated from a primary tumor and invade tissues to enter the blood circulation system, and are biological makers of cancer course tracking and cancer metastasis. Accordingly, the CTC detection can provide follow-up information of cancer metastasis and disease course, and can effectively evaluate the prognosis of patients and the effect of different cancer treatments. Moreover, the CTC detection can further accelerate the drug development of pharmaceutical companies. In recent years, there has been more and more related research and applications.

In addition, studies have found that nucleated red blood cells (NRBC) from fetuses are found in the blood of pregnant women, said nucleated red blood cells can be used as target cells for prenatal testing. The above method allows the fetal nucleated red blood cells (fNRBC) in the blood of the pregnant women to be obtained. The fNRBC is a fetus's cell with a complete biological signal, and can be used to assist the diagnosis of fetal gene or chromosomal abnormalities. Therefore, the fNRBC can be used as an alternative for invasive prenatal diagnosis method with high abortion rate such as amniocentesis and chorionic villus sampling (CVS).

However, the CTC or the fNRBC in blood is very scarce, so that it is very difficult to capture and screen target cells. In the related art, a centrifugation method, an immunomagnetic bead technology, and a microchannel technology are used to purify and separate rare cells. However, the centrifugation method may lose target cells caused by multiple liquid transfers. The immunomagnetic bead technology may easily damage rare cells by collisions, and the microchannel technology has a low cell capture rate due to the shear forces generated by channels, causing cells to accumulate into clumps. Moreover, the success rate of subsequent intensive experiments to isolate intact single rare cells from the immunomagnetic bead technology and the microchannel technology is extremely low.

Therefore, how to increase the capture rate of rare cells and to effectively obtain a single intact rare cell through improvement of a structural design for overcoming the above issues has become one of the important topics that need to be solved in this field.

SUMMARY OF THE DISCLOSURE

In response to the above-referenced technical inadequacies, the present disclosure provides a catcher, a capture device, and a method for capturing at least one target biological particle to effectively improve the issues associated with conventional catchers.

In one aspect, the present disclosure provides a capture device for being applied to capture a target biological particle from a specimen. The capture device includes two catchers and an adhesive layer that is gaplessly connected to the two catchers so as to jointly define a chamber. Each of the two catchers includes a base and a plurality of capture arms extending from the base and spaced apart from each other. Each of the capture arms has a free end portion configured to capture a target biological particle and a supporting segment connected between the free end portion and the base. The supporting segment of each of the capture arms is arranged in a projection space defined by orthogonally projecting the free end portion along a height direction onto the base. The capture arms of any one of the two catchers face toward another one of the two catchers, and the capture arms of the two catchers are arranged in the chambers. The capture device has an opening that is spatially communicated between the chamber and an external space that is located outside of the capture device, and the chamber is configured to accommodate a specimen through the opening. When the specimen is accommodated in the chamber, and the target biological particle is captured by two of the capture arms that are arranged adjacent to each other, the free end portion of any one of the two of the capture arms is attached with and carries the target biological particle so as to bend the corresponding supporting segment to have an elastic force, and a part of the target biological particle is trapped by the supporting segments of the two of the capture arms and is held by the elastic force.

In certain embodiments, the opening is formed in the adhesive layer, wherein the opening is tapered along a direction from an outer surface of the adhesive layer toward the chamber, so that any liquid in the chamber is unable to flow out of the chamber through the opening.

In certain embodiments, in each of the capture arms, the free end portion has an end surface arranged away from the supporting segment and at least one guiding surface connected to the end surface, wherein the at least one guiding surface of any one of the capture arms is configured to provide a lateral force to the corresponding supporting segment so as to tend to maintain the corresponding supporting segment in a curved shape when being attached with the target biological particle, and wherein the lateral force is non-parallel to the height direction.

In certain embodiments, in each of the capture arms, the free end portion has an end surface arranged away from the supporting segment and at least one guiding surface connected to the end surface, and wherein the guiding surfaces of at least two of the capture arms arranged adjacent to each other jointly define a notch that is configured to guide and trap the part of the target biological particle.

In certain embodiments, in each of the capture arms, an outer surface of the supporting segment is an etched lateral surface, so that the supporting segment is cuttable along a direction perpendicular to the height direction in a mechanical manner.

In certain embodiments, in each of the two catchers, the capture arms are distributed as a plurality of first patterned regions, any two of the first patterned regions adjacent to each other are spaced apart from each other by a first distance, any two of the capture arms of each of the first patterned regions adjacent to each other have an internal interval there-between, and the first distance is greater than the internal interval.

In one aspect, the present disclosure provides a method for capturing at least one target biological particle. The method includes a preparing step, an injection step, a turning over step, and a sampling step. The preparing step is implemented by providing the capture device. The injection step is implemented by injecting a specimen into the chamber through the opening until the chamber is fully filled with the specimen. The turning over step is implemented, after the injection step, by gradually turning over the capture device to exchange positions of the two catchers after waiting for a predetermined period of time. The sampling step is implemented by removing a liquid of the specimen from the chamber and cutting the supporting segments of each of the two catchers in a mechanical manner so as to separate the free end portions from the base and to obtain the free end portions of each of the two catchers.

In certain embodiments, in the sampling step, the liquid is removed from the chamber and the supporting segments of each of the two catchers are cut in the mechanical manner after destroying the adhesive layer to separate the two catchers from each other.

In certain embodiments, in the turning over step, the predetermined period of time is within a range of 5-15 minutes, wherein the sampling step is implemented, after the turning over step, by waiting for the predetermined period of time.

In one aspect, the present disclosure provides a catcher for being applied to capture at least one target biological particle from a specimen. The catcher includes a base and a plurality of capture arms extending from the base and spaced apart from each other. Each of the capture arms has a free end portion configured to capture a target biological particle and a supporting segment connected between the free end portion and the base. The supporting segment of each of the capture arms is arranged in a projection space defined by orthogonally projecting the free end portion along a height direction onto the base. When the target biological particle is captured by two of the capture arms that are arranged adjacent to each other, the free end portion of any one of the two of the capture arms is attached with and carries the target biological particle so as to bend the corresponding supporting segment to have an elastic force, and a part of the target biological particle is trapped by the supporting segments of the two of the capture arms and is held by the elastic force.

In certain embodiments, in each of the capture arms, the free end portion has an end surface arranged away from the supporting segment and at least one guiding surface connected to the end surface, wherein the at least one guiding surface of any one of the capture arms is configured to provide a lateral force to the corresponding supporting segment so as to tend to maintain the corresponding supporting segment in a curved shape when being attached with the target biological particle, and wherein the lateral force is non-parallel to the height direction.

In certain embodiments, in each of the capture arms, the supporting segment includes a plurality of elongated parts connected to each other, and each of the elongated arms has two opposite ends respectively connected to the base and the free end portion, and wherein each of the supporting segments is bendable with respect to the height direction by a swing angle that is less than or equal to 5 degrees.

In certain embodiments, the capture arms are distributed to form a plurality of first patterned regions, any two of the first patterned regions adjacent to each other are spaced apart from each other by a first distance, any two of the capture arms of each of the first patterned regions adjacent to each other have an internal interval there-between, and the first distance is greater than the internal interval.

In certain embodiments, the supporting segment of any one of the capture arms has a maximum width greater than the internal interval, and the free end portion of any one of the capture arms has a maximum width greater than the internal interval.

In certain embodiments, the capture arms are further distributed to form a second patterned region arranged between any two of the first patterned regions that are spaced apart from each other by a distance more than two times of the first distance, and wherein each of the second patterned regions and any one of the first patterned regions adjacent thereto are spaced apart from each other by the first distance, and any two of the capture arms adjacent to each other and belonging to any one of the second patterned regions have the internal interval there-between.

In certain embodiments, the capture arms are further distributed to form a plurality of second patterned regions, wherein each of the second patterned regions is surrounded by at least three of the first patterned regions, and is spaced apart from any one of the first patterned regions adjacent thereto by the first distance, and wherein any two of the capture arms adjacent to each other and belonging to any one of the second patterned regions have the internal interval there-between.

In certain embodiments, any two of the second patterned regions adjacent to each other are spaced apart from each other by a second distance greater than the first distance, and wherein the second distance is less than an outer diameter of any one of the first patterned regions.

In certain embodiments, each of the first patterned regions is an N-sided polygon, and each of the second patterned regions is an M-sided polygon, and wherein N and M are positive integers, and N is greater than M.

In certain embodiments, the capture arms are in a matrix arrangement, and any two of the capture arms adjacent to each other have an internal interval there-between.

In certain embodiments, in each of the capture arms, an outer surface of the supporting segment is an etched lateral surface, so that the supporting segment is cuttable along a direction perpendicular to the height direction in a mechanical manner.

Therefore, the quasi-soft catcher and the method of the present disclosure are provided to increase the success rate of capturing single target biological particle and to separate each of the target biological particles from the quasi-soft catcher intact by the technical solution of "the protruding structures extend from the board surface and regularly arranged, each of the protruding structures includes an outer portion configured to touch at least one target biological particle and an inner portion that is connected between the board surface and the outer portion, a structural strength of the inner portion of each of the protruding structures is less than that of the corresponding outer portion, and the board surface has an interspace region arranged outside of the protruding portions, and the interspace region occupies 20-80% of the board surface."

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

Figure 1:
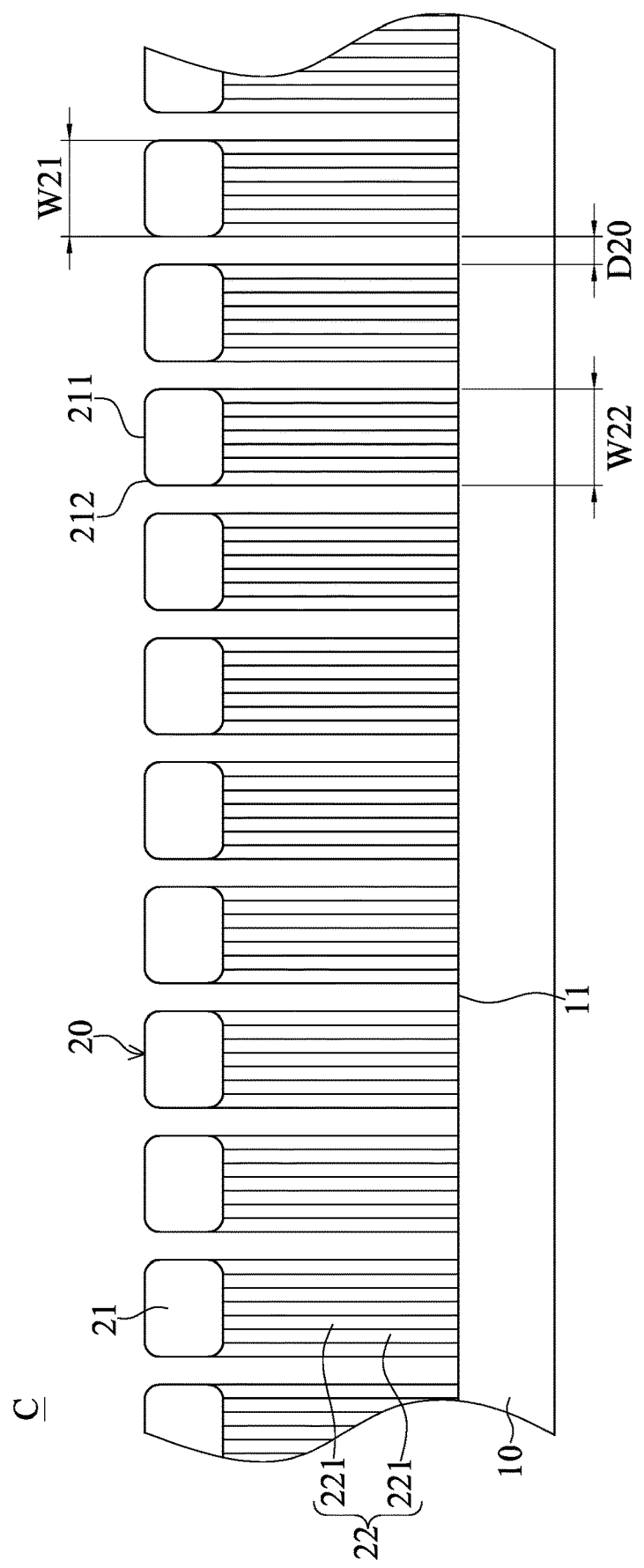
FIG. 1 is an enlarged side view of a quasi-soft catcher according to a first configuration of a first embodiment of the present disclosure.
Figure 2:
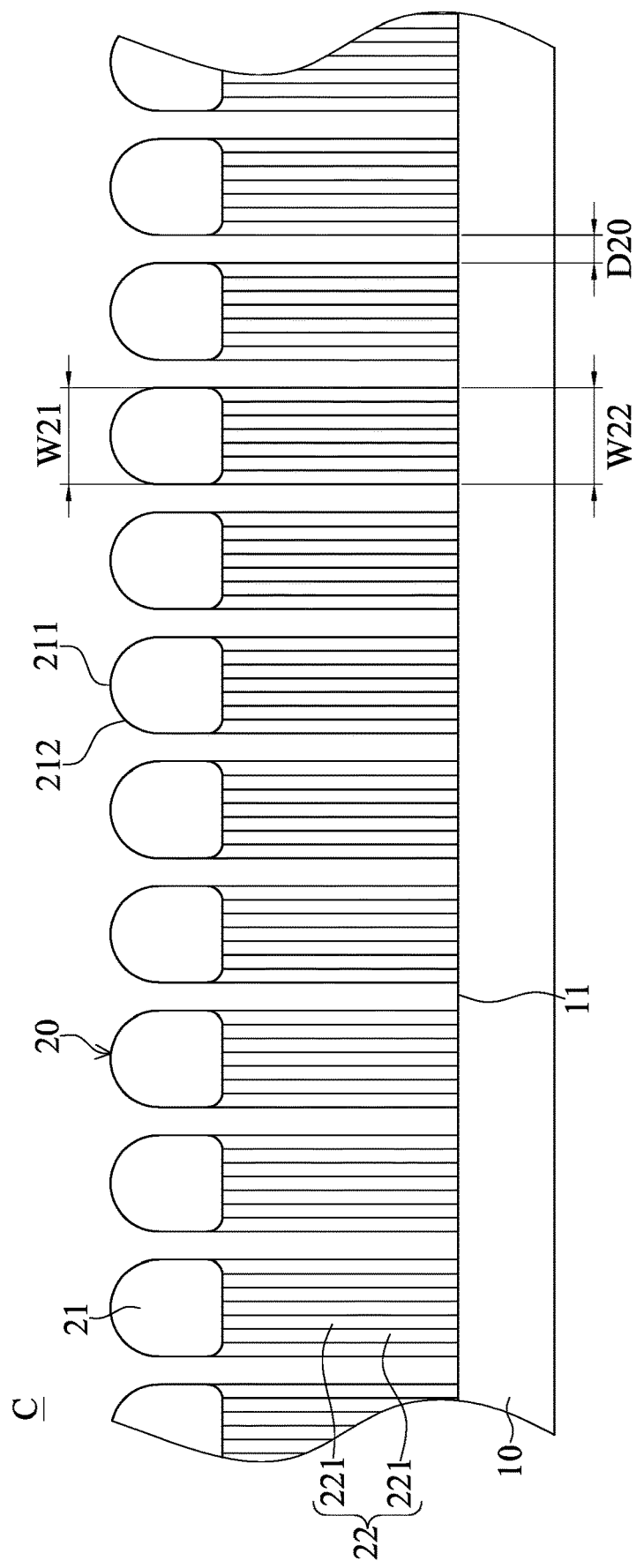
FIG. 2 is an enlarged side view of the quasi-soft catcher according to a second configuration of the first embodiment of the present disclosure.
Figure 3:
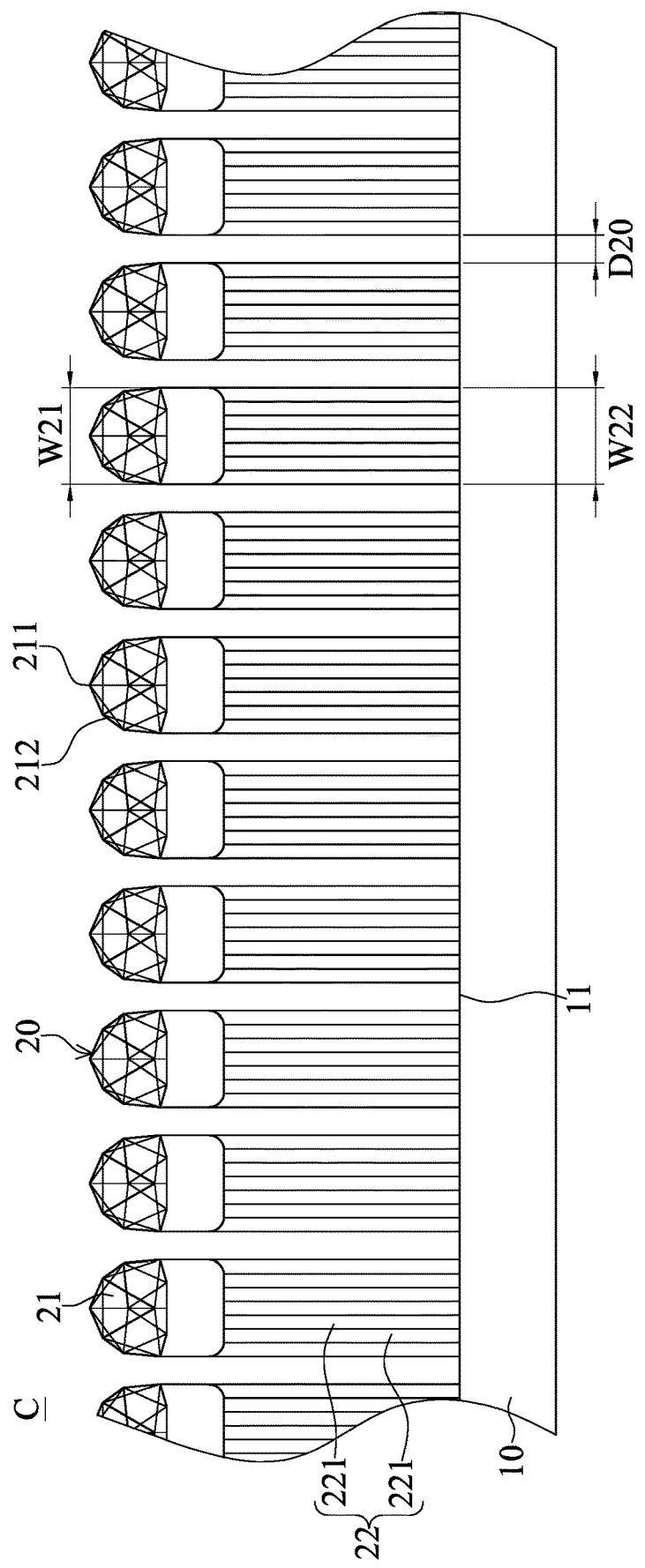
FIG. 3 is an enlarged side view of the quasi-soft catcher according to a third configuration of the first embodiment of the present disclosure.
Figure 4:
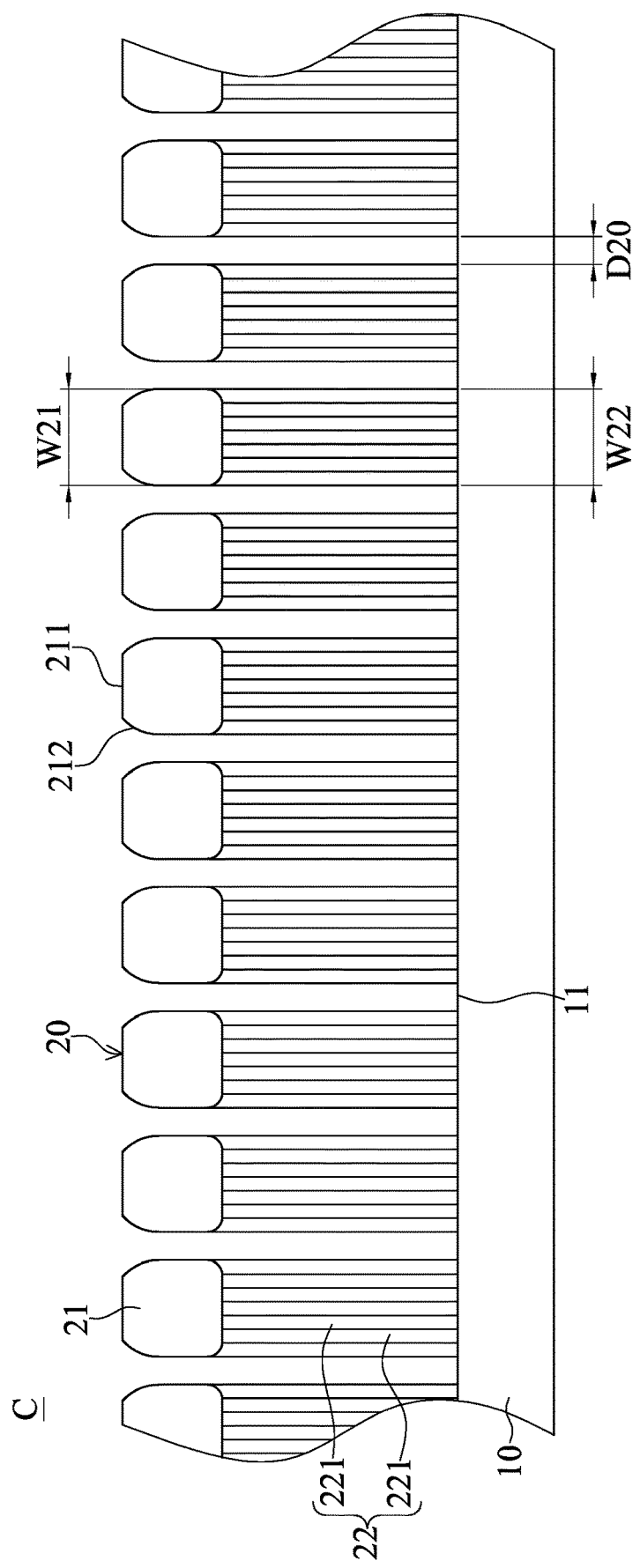
FIG. 4 is an enlarged side view of the quasi-soft catcher according to a fourth configuration of the first embodiment of the present disclosure.
Figure 5:
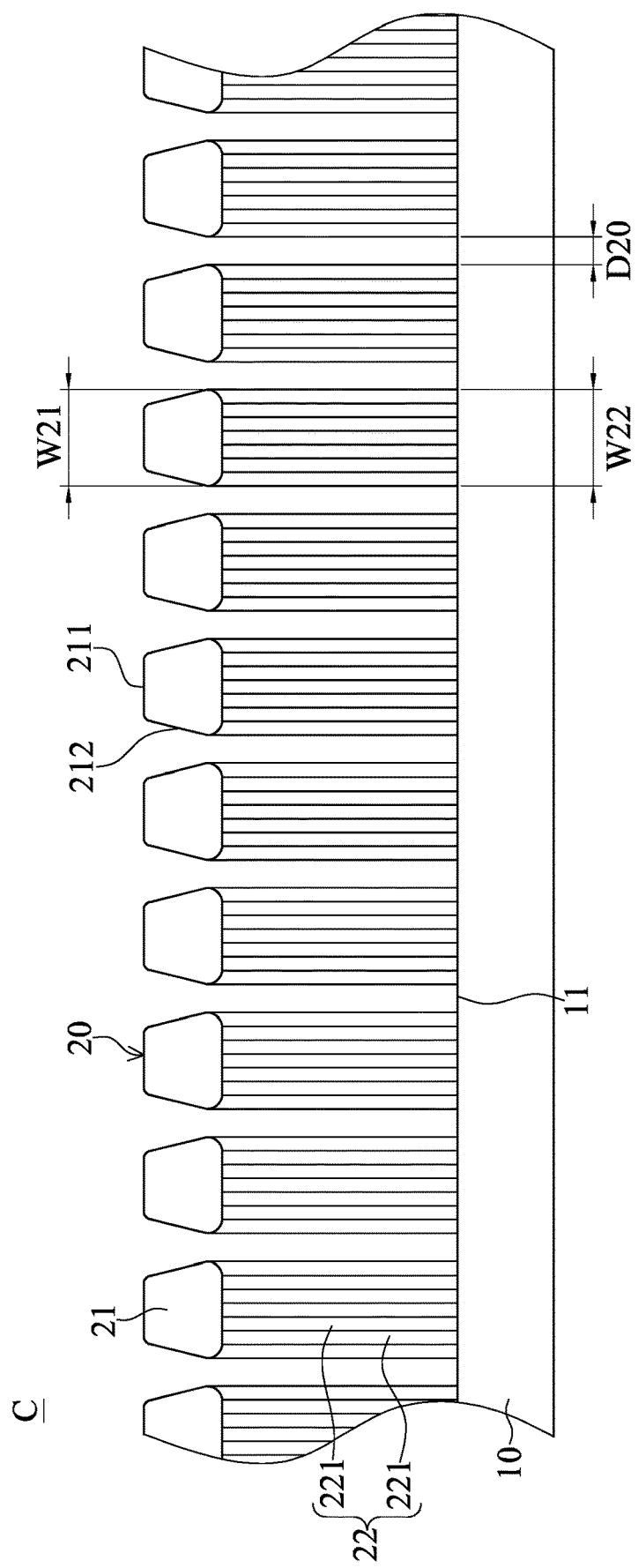
FIG. 5 is an enlarged side view of the quasi-soft catcher according to a fifth configuration of the first embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

First Embodiment

Figure 6:
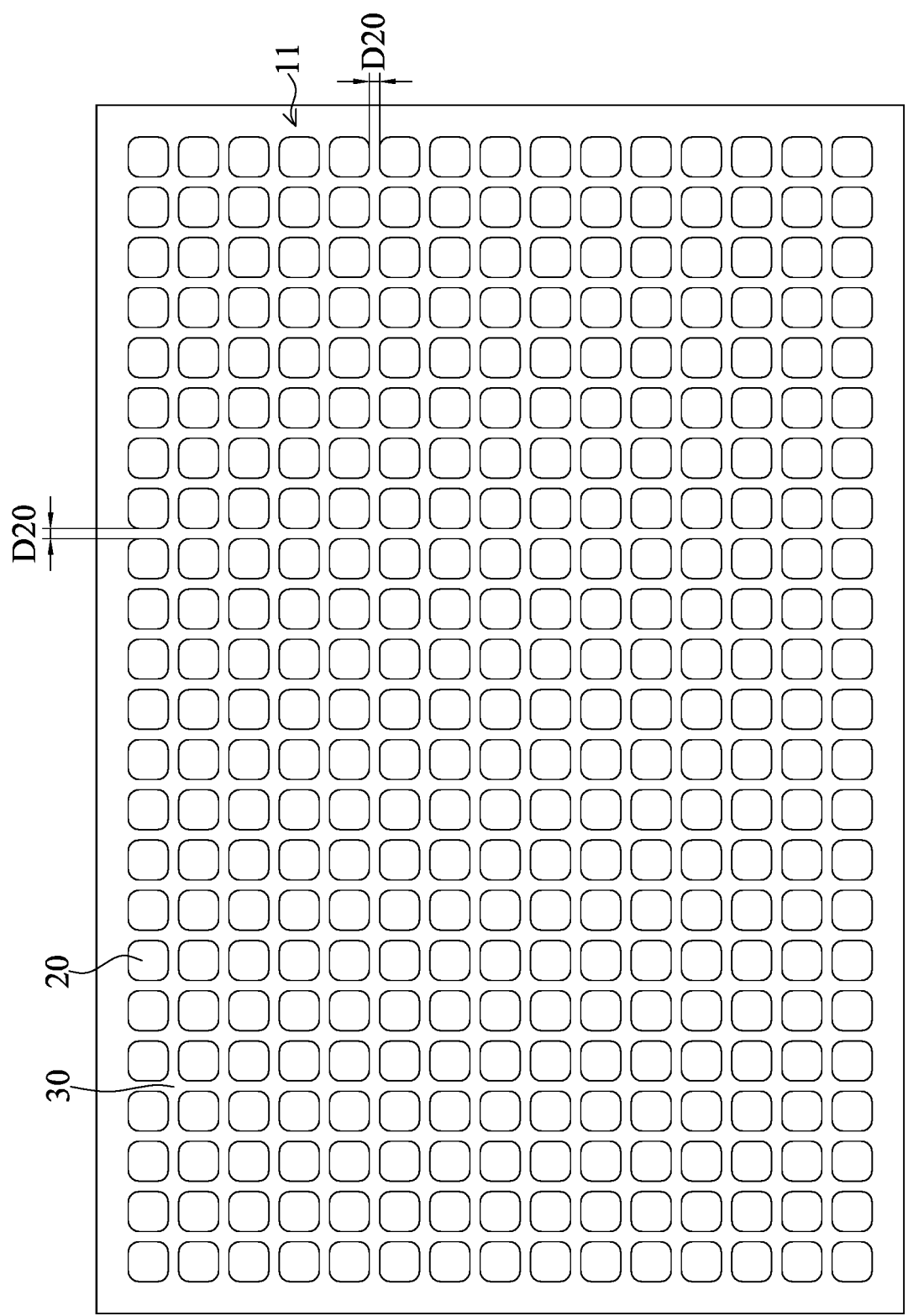
FIG. 6 is a top view showing a plurality of protruding structures of the quasi-soft catcher distributed in a first arrangement according to the first embodiment of the present disclosure.
Figure 7:
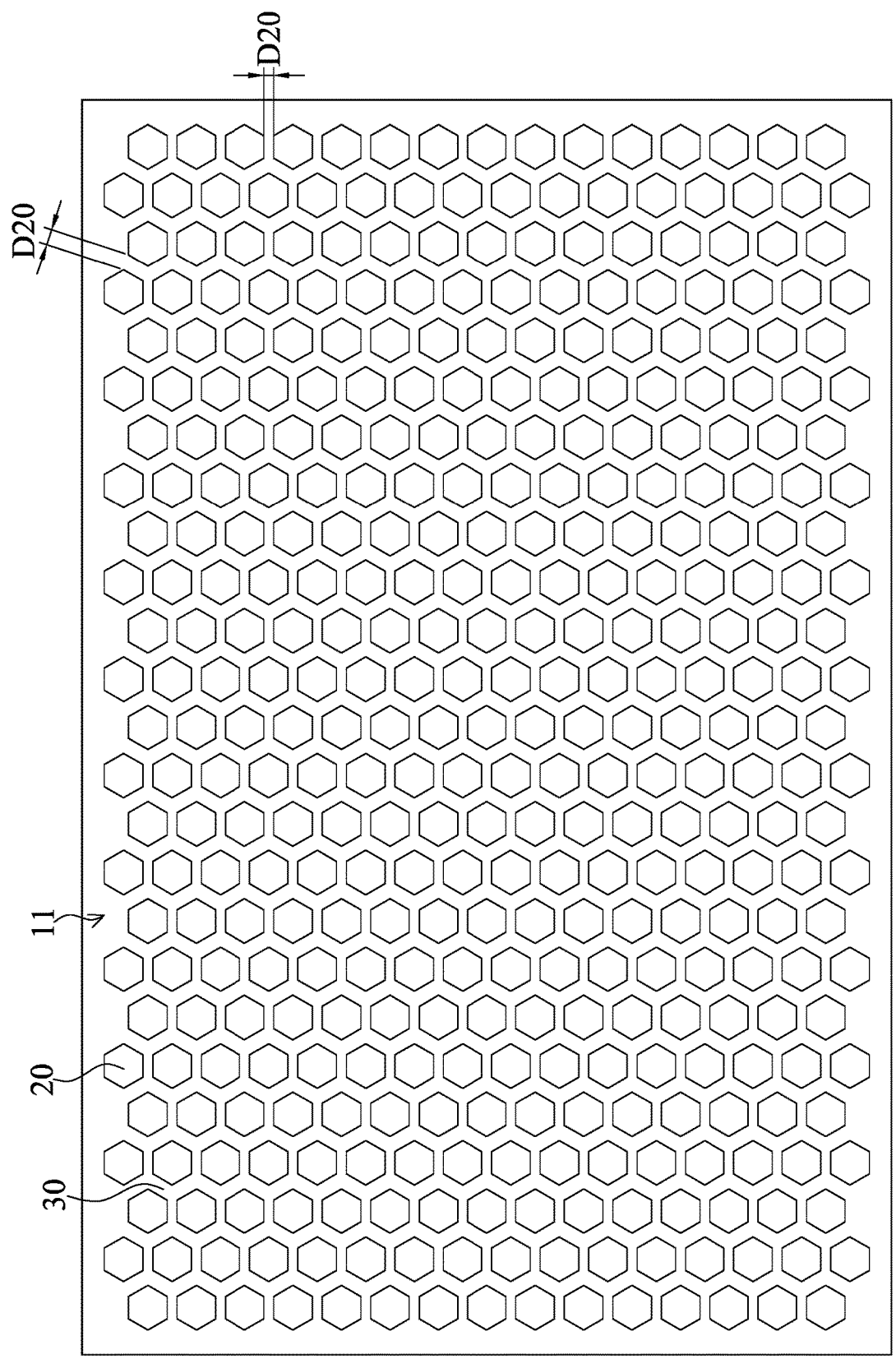
FIG. 7 is a top view showing the protruding structures of the quasi-soft catcher distributed in a second arrangement according to the first embodiment of the present disclosure.

Referring to FIG. 1, FIG. 6, and FIG. 7, a first embodiment of the present disclosure provides a quasi-soft catcher C that is configured to capture at least one target biological particle from a specimen. The quasi-soft catcher C includes a base 10 and a plurality of protruding structures 20. The quasi-soft catcher C can be made of a semi-conductor material or a biocompatible material. For example, the semi-conductor material can be a silicon or a glass, and the biocompatible material can be a polydimethylsiloxane (PDMS), a poly-methyl methacrylate (PMMA), a polycarbonates (PC), or a polystyrene (PS), but the present disclosure is not limited thereto.

As shown in FIG. 1, the base 10 has a board surface 11, and the protruding structures 20 are regularly arranged on the board surface 11. Each of the protruding structures 20 can be a cylinder, a blunt cone, a polygonal cylinder, or a blunt polygon. Each of the protruding structures 20 includes an outer portion 21 configured to touch the target biological particle and an inner portion 22 that is connected between the board surface 11 and the outer portion 21. Moreover, a structural strength of the inner portion 22 is less than that of the outer portion 21, and the inner portion 22 can be destroyed due to the structural strength thereof. As shown in FIG. 1 to FIG. 5, it should be noted that the outer portion 21 of each of the protruding structures 20 can be in a cylindrical shape, dome shape, a conical frustum shape, or a pyramidal frustum shape, and an outer surface of each of the outer portions 21 can be a rough surface or a smooth surface. In other words, each of the outer portions 21 can be adjusted or changed according to practical requirements so as to suitably capture the target biological particle. Moreover, the inner portion 22 of each of the protruding structures 20 has at least one structural weakness part that can be directly destroyed in a mechanical manner. In the following description, the protruding structure 20 can be cut from the structural weakness part by an obtaining device, so that the outer portion 21 is separated from the base 10. In the present embodiment, the protruding structures 20 are made of a silicon crystal substrate and are formed by a semiconductor lithography in an etching manner, so that each of the inner portions 22 has a loose structure due to the etching manner and has a structural density less than that of the inner portion 21. Accordingly, in each of the protruding structures 20, the inner portion 22 is more easily destroyed than the outer portion 21, but the present disclosure is not limited thereto.

As shown in FIG. 1, FIG. 6, and FIG. 7, the board surface 11 has an interspace region 30 arranged outside of the protruding portions 20. That is to say, a region of the board surface 11 not connected to any one of the protruding portions 20 is defined as the interspace region 30. Moreover, the interspace area 30 in the present embodiment occupies 20-80% of the board surface 11. Specifically, in order to have the interspace region 30 be a specific size, any two of the outer portions 21 of the protruding structures 20 adjacent to each other can have an interval there-between that is within a range of 0.2-2 µm, and the outer portion 21 of each of the protruding structures 20 can have an outer diameter within a range of 0.6-2 µm. In addition, with consideration to the ability of the protruding structures 20 to capture the target biological particle and the convenience of cutting the protruding structures 20, the outer portion 21 of each of the protruding structures 20 has a height that can be within a range of 0.1-5 µm, and the inner portion 22 of each of the protruding structures 20 has a height that can be within a range of 2-15 µm. However, the quasi-soft catcher C of the present disclosure is not limited to the above description.

It should be noted that the protruding structures 20 of the quasi-soft catcher C in the present embodiment is used in cooperation with the interspace region 30 by being regularly arranged so as to be jointly formed as a quasi-soft structure. Accordingly, when the quasi-soft catcher C touches the specimen, the target biological particle can be effectively attached onto the outer portions 21 of the protruding structures 20 without being punctured or scratched.

FIG. 6 is provided to show the protruding structures 20 of the quasi-soft catcher C distributed in a first arrangement. As shown in FIG. 6, the protruding structures 20 are formed on the board surface 11 of the base 10 in a matrix arrangement, and each of the protruding structures 20 is a square cylinder. FIG. 7 is provided to show the protruding structures 20 of the quasi-soft catcher C distributed in a second arrangement. As shown in FIG. 6, the protruding structures 20 are formed on the board surface 11 of the base 10 in a matrix arrangement and are staggered with each other, and each of the protruding structures 20 is a hexagonal cylinder.

In addition, each of the protruding structures 20 can be modified with a molecular cluster (e.g., antibodies, receptors, or specific markers) that is configured to only be coupled with the target biological particle, but the present disclosure is not limited thereto.

Second Embodiment

Figure 8:
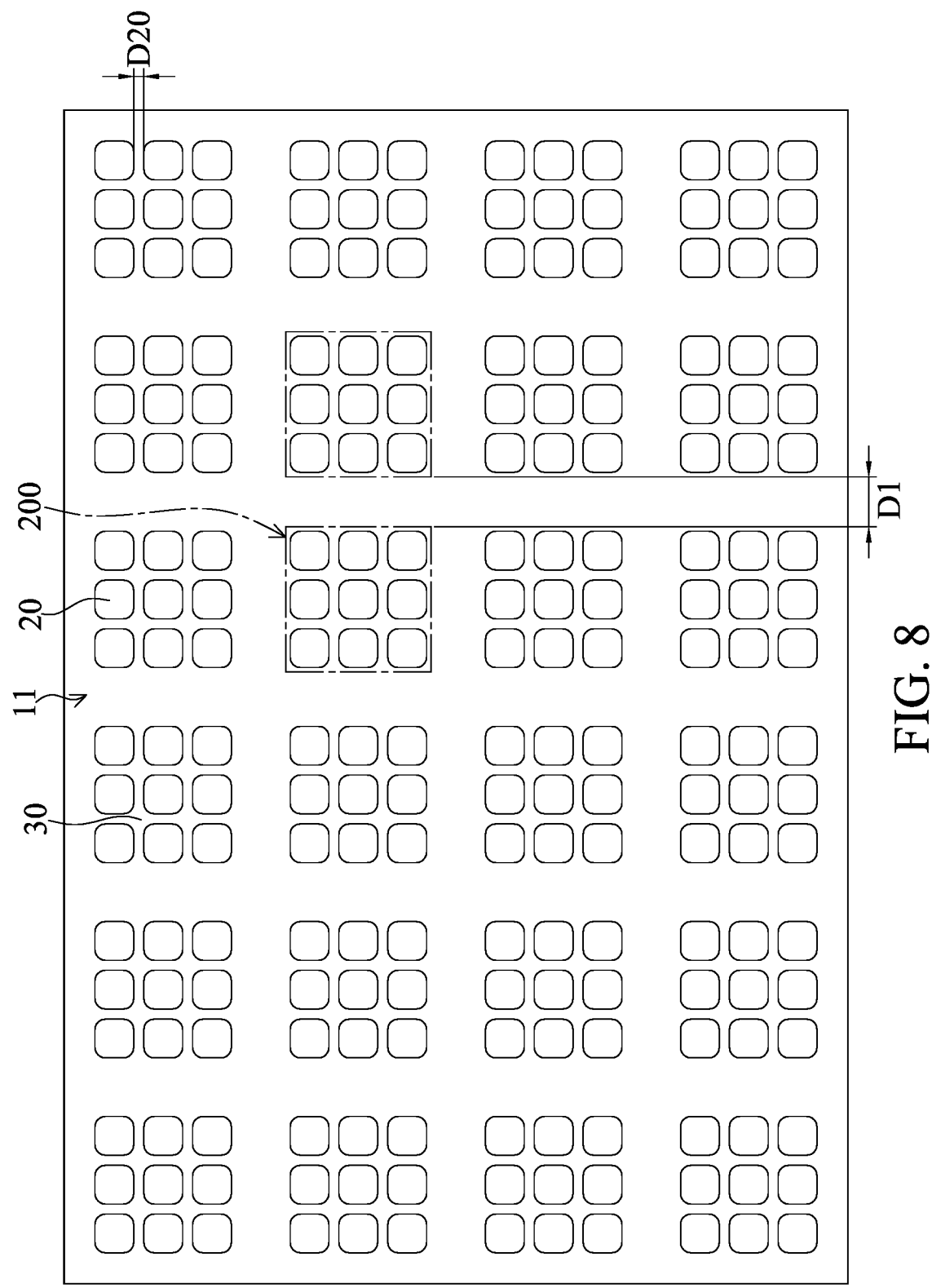
FIG. 8 is a top view showing a plurality of protruding structures of a quasi-soft catcher distributed in a first arrangement according to a second embodiment of the present disclosure.
Figure 9:
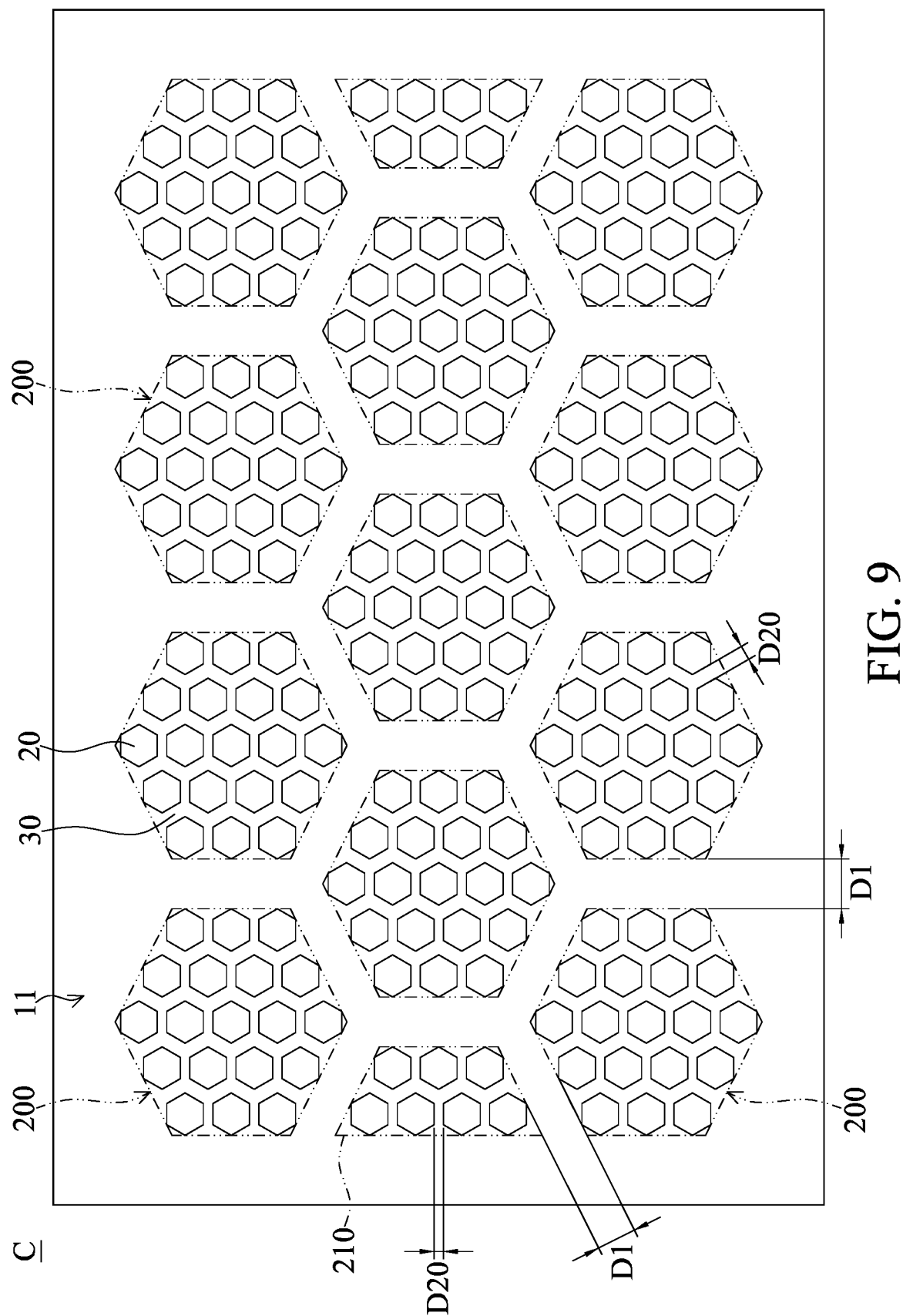
FIG. 9 is a top view showing the protruding structures of the quasi-soft catcher distributed in a second arrangement according to the second embodiment of the present disclosure.
Figure 10:
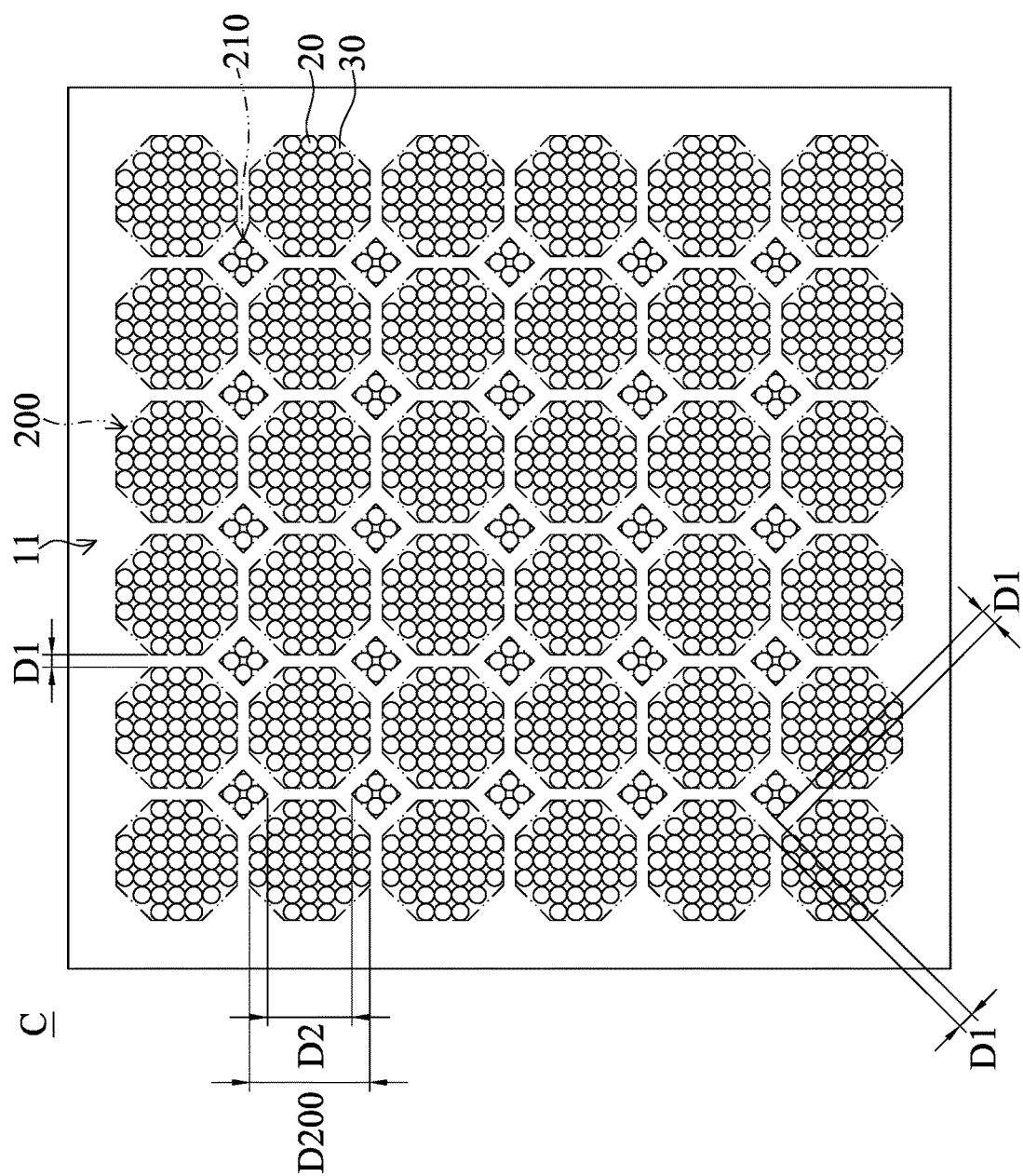
FIG. 10 is a top view showing the protruding structures of the quasi-soft catcher distributed in a third arrangement according to the second embodiment of the present disclosure.

Referring to FIG. 8 to FIG. 10, a second embodiment of the present disclosure is similar to the first embodiment of the present disclosure. For the sake of brevity, descriptions of the same components in the first and second embodiments of the present disclosure will be omitted, and the following description only discloses different features between the first and second embodiments.

In the quasi-soft catcher C of the present embodiment, part of the protruding structures 20 on the board surface 11 are distributed as a plurality of first structural groups 200, and each of the first structural groups 200 defines a capture region having an N-sided polygon with a shape corresponding to the target biological particle, and N is an integer larger than or equal to three. Preferably, 8≤N≤12. As shown in FIG. 8, the protruding structures 20 of any one of the first structural groups 200 are distributed in a quadrilateral region that is defined as the capture region.

It should be noted that the size of any one of the first structural groups 200 can be adjusted or changed according to the size of the target biological particle. For example, if the target biological particle is a CTC or a general cell, an outer diameter of the capture region would be within a range of 10-100 µm. If the target biological particle is an NRBC, the outer diameter of the capture region would be within a range of 6-9 µm. If the target biological particle is a bacterium, the outer diameter of the capture region would be within a range of 2-3 µm. However, the quasi-soft catcher C of the present disclosure is not limited to the above description.

Furthermore, in the quasi-soft catcher C of the present embodiment, another part of the protruding structures 20 on the board surface 11 are distributed as at least one second structural group 210, and the at least one second structural group 210 defines a buffering region arranged adjacent to at least one of the capture regions. Moreover, an area of the buffering region is smaller than that of each of the capture regions. It should be noted that the buffering region is not intended to capture the target biological particle, and that the area of the buffering region defined by the at least one second structural group 210 can be smaller than that of each of the capture regions defined by the corresponding first structural group 200.

Specifically, the second structural group 210 is provided to prevent the target biological particle from falling into a gap that is defined by the first structural groups 200 adjacent to each other. FIG. 9 is provided to show the protruding structures 20 of the quasi-soft catcher C distributed in one arrangement. As shown in FIG. 9, part of the protruding structures 20 on the board surface 11 are distributed as a plurality of first structural groups 200 each having a hexagon contour, and another part of the protruding structures 20 on the board surface 11 are distributed as two second structural groups 210 each having a trapezoidal contour. FIG. 10 is provided to show the protruding structures 20 of the quasi-soft catcher C distributed in another arrangement. As shown in FIG. 10, part of the protruding structures 20 on the board surface 11 are distributed as a plurality of first structural groups 200 each having an octagonal contour, and another part of the protruding structures 20 on the board surface 11 are distributed as a plurality of second structural groups 210 each having a rhombic contour.

Third Embodiment

Figure 11:
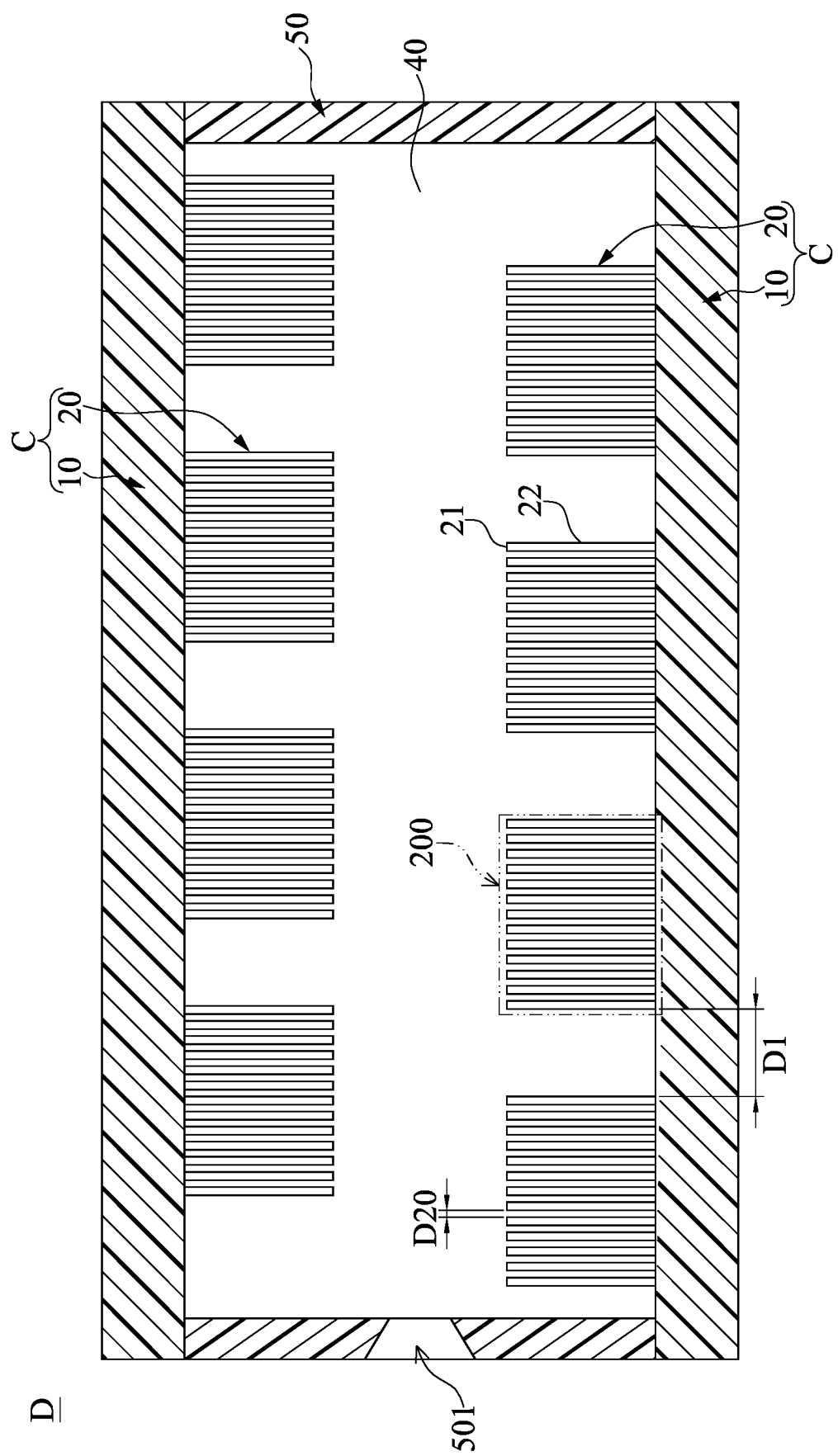
FIG. 11 is a cross-sectional view showing a quasi-soft capture device according to a third embodiment of the present disclosure.

Referring to FIG. 11, a third embodiment of the present disclosure provides a quasi-soft capture device D. In the present embodiment, the quasi-soft capture device D includes two quasi-soft catchers C identical to that of the first embodiment or the second embodiment. Moreover, the two quasi-soft catchers C are connected to each other and have a chamber 40 there-between that is configured to receive a specimen.

Fourth Embodiment

Figure 12:
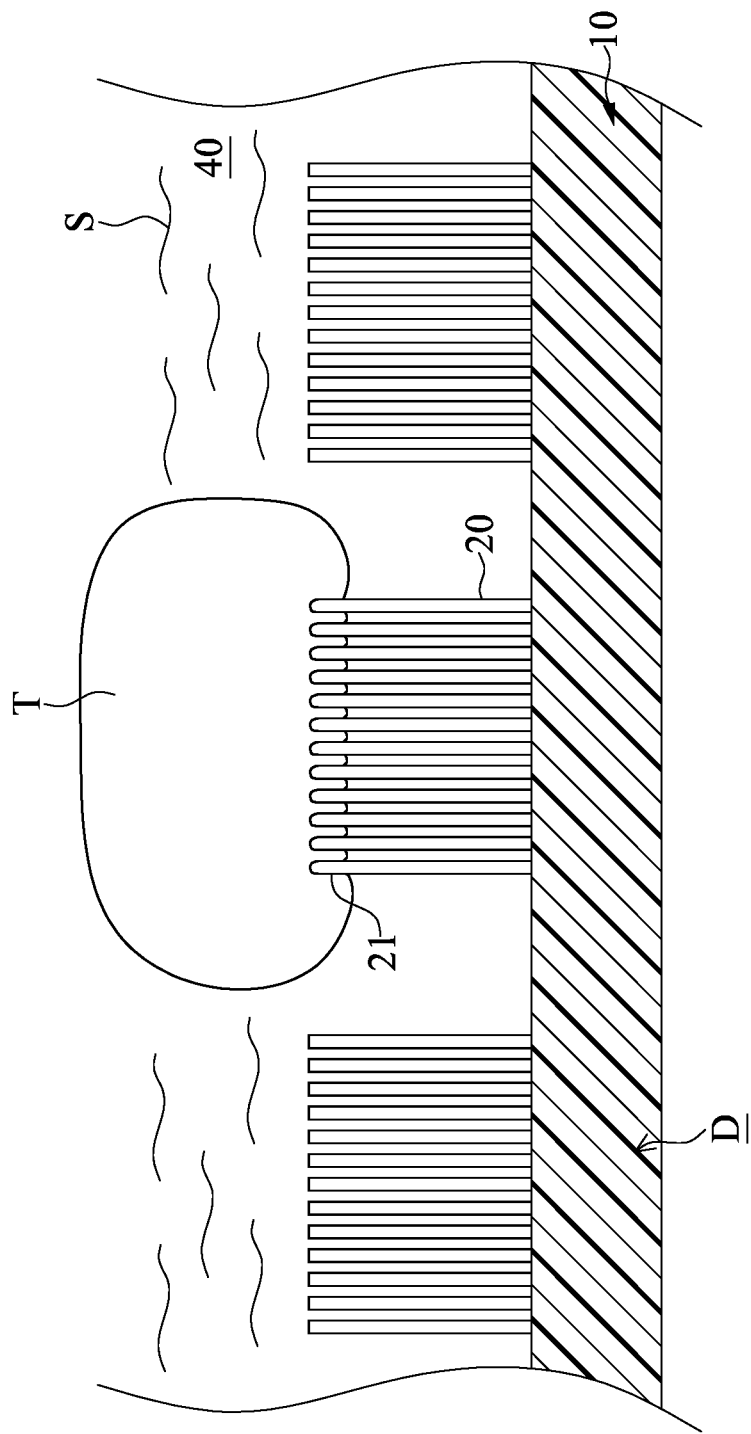
FIG. 12 is a schematic view showing a method implemented to screen and separate a target biological particle from a specimen according to the present disclosure.
Figure 13:
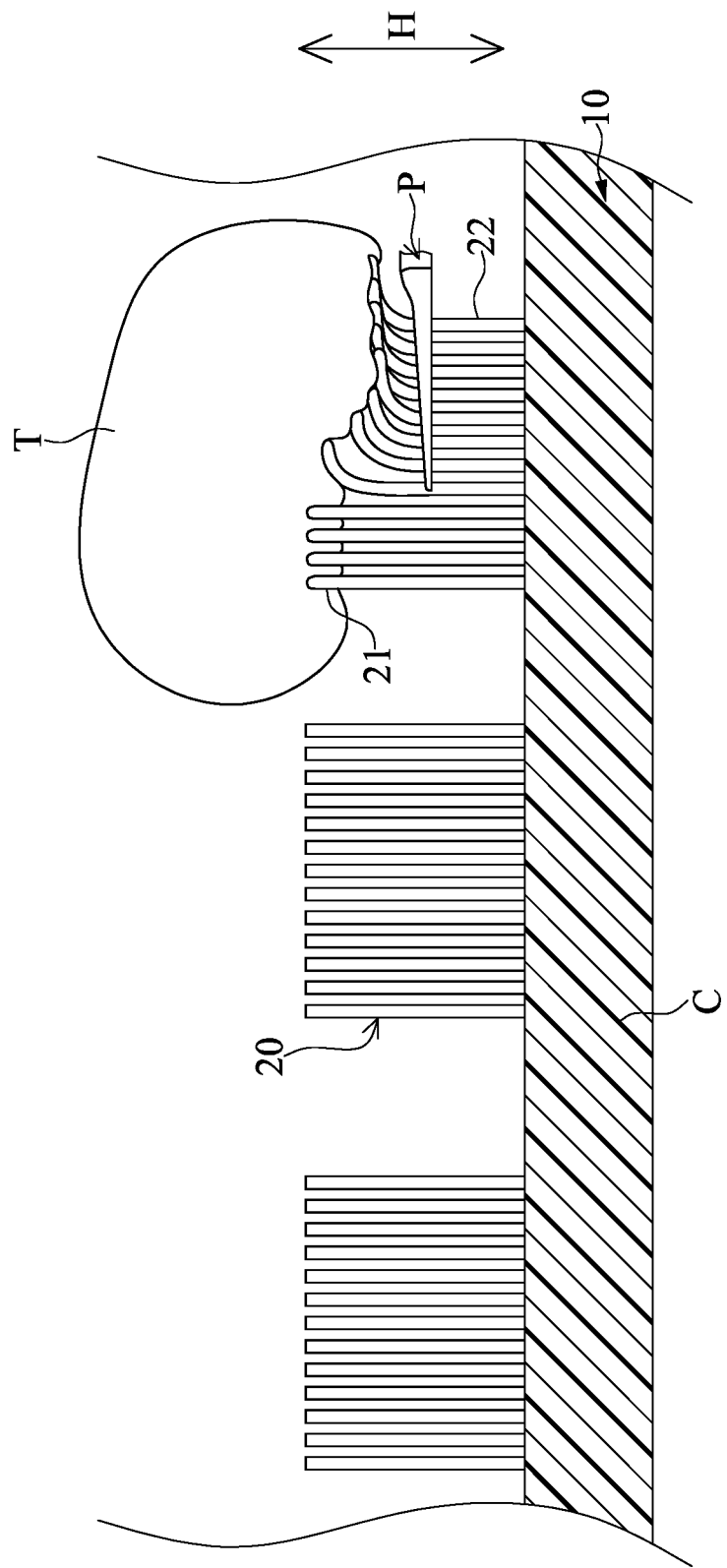
FIG. 13 is a schematic view showing the method implemented to obtain the target biological particle from the quasi-soft capture device according to the present disclosure.

Referring to FIG. 12 and FIG. 13, a fourth embodiment of the present disclosure provides a method for using the quasi-soft capture device D as disclosed in the third embodiment. The method of the present embodiment includes step as follows.

As shown in FIG. 12, a specimen S is put into the chamber 40 of the quasi-soft capture device D. The specimen S includes a liquid and at least one target biological particle T distributed in the liquid. In a specific embodiment, the two quasi-soft catchers C are connected and sealed to each other by an adhesive layer that has an injection opening, and the specimen S is injected into the chamber 40 of the quasi-soft capture device D through the injection opening until the chamber 40 is fully filled with the specimen S. The specimen S may be a liquid specimen from an animal or a plant (e.g., blood, urine, lymph, saliva, or a tissue extract of a plant). The target biological particle T can be a specific cell, microorganism, or protein. For example, the target biological particle T can be circulating tumor cells (CTC), fetal trophoblast cells, fetal nuclear red blood cells (fNRBC), virus particles, bacteria, or antigens. However, the method of the present disclosure is not limited to the above description.

Moreover, the specimen S is manipulated to flow within the chamber 40 so as to allow the at least one target biological particle T to be captured by the quasi-soft capture device D (e.g., at least one of the two quasi-soft catchers C). The outer portions 21 of the protruding structures 20 of the quasi-soft capture device D are configured to capture the at least one target biological particle T by an interaction. In addition, the number of the at least one target biological particle T captured by the quasi-soft capture device D can be more than one.

Specifically, the flowing of the specimen S in the chamber 40 can be implemented by slowly turning over the quasi-soft capture device D through a driving device or a carrier, or can be implemented by using a non-uniform electric field to generate a dielectrophoresis phenomenon. Since any one of the two quasi-soft catchers C of the quasi-soft capturing device D in the present disclosure is a quasi-soft structure, the target biological particles T in the specimen S can be effectively perturbed in the chamber 40 without destroying the integrity of any one of the target biological particles T. Accordingly, the biological signal of the any one of the target biological particles T can be prevented from being lost due to the damage of the target biological particles T caused by the shearing force. In one specific embodiment, the quasi-soft capturing device D can be placed and let sit for 10 minutes, and then after being turned over to the other side, the quasi-soft capturing device D is placed and let sit for another 10 minutes, so that each of the two quasi-soft catchers C can effectively capture the target biological particles T.

It should be noted that the outer portion 21 of each of the protruding structures 20 can be modified with a molecular cluster that is configured to only be coupled with the target biological particle T. In other words, the target biological particle T and the molecular cluster can be bonded by a specific binding, so that the target biological particle T would be easily captured by the outer portions 21 of the protruding structures 20. In one specific embodiment, the target biological particles T in the specimen S can be bound to the biotin-containing antibody first, and the outer portion 21 of each of the protruding structures 20 can be modified with streptavidin specific to biotin streptavidin, so that when biotin and streptavidin are specifically bonded, the target biological particles T would stay on the capture region formed by the first structural groups 200.

Next, the liquid of the specimen S is removed. Specifically, the quasi-soft capture device D can be further rinsed with a solution (e.g., PBS) that is suitable in this technical field so as to ensure that only the target biological particles T are on the quasi-soft catchers C. According to practical requirements, the target biological particles T can be fluorescently stained to facilitate the confirmation of the location of the target biological particles T. In the present embodiment, after capturing the target biological particles T, the two quasi-soft catchers C can be separated from each other.

Finally, as shown in FIG. 13, an obtaining device P is used to cut the inner portions 22 of the protruding structures 20 that capture the target biological particle T, thereby separating the target biological particle T from the quasi-soft capture device D. Specifically, the obtaining device P is used to directly destroy the protruding structures 20 (i.e., to cut the protruding structures 20) in a physical manner, so that the outer portions 21 and the captured target biological particle T are separated from the base 10. Accordingly, the target biological particle T can be separated from the quasi-soft catcher C intact.

Quasi-Soft Catcher

The following description describes the quasi-soft catcher C of the present disclosure from different angles according to the above embodiments. The quasi-soft catcher C is also referred to as a catcher C. Each of the protruding structures 20 of the catcher C is an elastic structure, and as a result, the protruding structure 20 is referred to as a capture arm 20.

As shown in FIG. 13, the capture arms 20 extend from the base 10 and are spaced apart from each other. Each of the capture arms 20 is in an elongated shape, and includes a free end portion 21 configured to capture the target biological particle T and a supporting segment 22 connected between the free end portion 21 and the base 10. A length of the free end portion 21 is less than that of the supporting segment 22 (e.g., the length of the free end portion 21 is 10-35% of the length of the supporting segment 22). A width of the supporting segment 22 is affected by a lateral etching, so that the width of the supporting segment 22 is less than that of the free end portion 21. In other words, the supporting segment 22 is arranged in a projection space defined by orthogonally projecting the free end portion 21 along a height direction H onto the base 10. It should be noted that the height direction H in the present embodiment is perpendicular to the base 10 or is parallel to a longitudinal direction of the capture arm 20, but the present disclosure is not limited thereto.

Moreover, when the target biological particle T is captured by two of the capture arms 20 of the catcher C that are arranged adjacent to each other, the free end portion 21 of any one of the two of the capture arms 20 is attached with and carries the target biological particle T so as to bend the corresponding supporting segment 22 to have an elastic force, and a part of the target biological particle T is trapped by the supporting segments 22 of the two of the capture arms 20 and is held by the elastic force, but the present disclosure is not limited thereto. For example, though the supporting segments 22 can be not bent (shown in FIG. 12), the target biological particle T can still be trapped by at least two of the supporting segments 22 adjacent to each other.

Accordingly, the catcher C can effectively use gaps between the bent supporting segments 22 of the capture arms 20 to capture or retain the target biological particle T by forming the capture arms 20 having elastic property, thereby preventing the target biological particle T from being damaged by the catcher C. The elastic property of the capture arm 20 and the bending level of the supporting segment 22 can be adjusted or changed according to design requirements. For example, the capture arm 20 is swingable relative to the base 10, and the capture arm 20 is bendable with respect to the height direction H by a swing angle that is less than or equal to 5 degrees. In other words, as long as the position of the capture arm 20 can be changed with respect to the base 10, the capture arm 20 can be regarded as having the elastic property.

It should be noted that each of the capture arms 20 of the catcher C is formed as an elongated structure by etching, so that in each of the capture arms 20, an outer surface of the supporting segment 22 is an etched lateral surface. Accordingly, the supporting segment 22 of each of the capture arms 20 is cuttable along a direction perpendicular to the height direction H in a mechanical manner.

The supporting segment 22 of the capture arm 20 shown in FIG. 13 is a single elongated structure, but the present disclosure is not limited thereto. As shown in FIG. 1 to FIG. 5, in each of the capture arms 20, the supporting segment 22 includes a plurality of elongated parts 221 connected to each other, and each of the elongated arms 221 has two opposite ends respectively connected to the base 10 and the free end portion 21.

Moreover, in each of the capture arms 20, the free end portion 21 has an end surface 211 arranged away from the supporting segment 22 and at least one guiding surface 212 connected to the end surface 211. The at least one guiding surface 212 of any one of the capture arms 20 is configured to provide a lateral force to the corresponding supporting segment 22 so as to tend to maintain the corresponding supporting segment 22 in a curved shape when being attached with the target biological particle T, in which the lateral force is non-parallel to the height direction H. In other words, the guiding surfaces 212 of at least two of the capture arms 20 arranged adjacent to each other jointly define a notch (not labeled) that is lower than the end surface 211 and is configured to guide and trap the part of the target biological particle T, thereby preventing the target biological particle T from being damaged by the catcher C. In addition, in other embodiments of the present disclosure, when the supporting segments 22 are not bent, the notch defined by the guiding surfaces 212 adjacent to each other can be used to guide and trap the part of the target biological particle T.

As shown in FIG. 6 and FIG. 7, the capture arms 20 of the catcher C can be in a matrix arrangement, and any two of the capture arms 20 adjacent to each other have an internal interval D20 there-between, but the present disclosure is not limited thereto. Moreover, the supporting segment 22 of any one of the capture arms 20 has a maximum width W22 (shown in FIG. 1 to FIG. 5) greater than the internal interval D20, and the free end portion 21 of any one of the capture arms 20 has a maximum width W21 (shown in FIG. 1 to FIG. 5) greater than the internal interval D20, but the present disclosure is not limited thereto.

In addition, as shown in FIG. 8, the capture arms 20 are distributed to form a plurality of first patterned regions 200, and edges of each of the first patterned regions 200 in the present embodiment are substantially overlapped with outer edges of the corresponding capture arms 20. Moreover, any two of the first patterned regions 200 adjacent to each other are spaced apart from each other by a first distance D1, any two of the capture arms 20 of each of the first patterned regions 200 adjacent to each other have the internal interval D20 there-between, and the first distance D1 is greater than the internal interval D20.

As shown in FIG. 9 and FIG. 10, the capture arms 20 can be further distributed to form a plurality of second patterned regions 210. Each of the second patterned regions 210 is surrounded by at least three of the first patterned regions 200, and is spaced apart from any one of the first patterned regions 200 adjacent thereto by the first distance D1. Any two of the capture arms 20 adjacent to each other and belonging to any one of the second patterned regions 210 have the internal interval D20 there-between.

In other words, any one of the second patterned regions 210 is arranged between two of the first patterned regions 200 (e.g., the two first patterned regions 200 respectively located at an upper left corner and a lower left corner of FIG. 9, or the two first patterned regions 200 facing each other along a slanting direction of FIG. 10) that are spaced apart from each other by a distance more than two times of the first distance D1. Moreover, each of the second patterned regions 210 and any one of the first patterned regions 200 adjacent thereto are spaced apart from each other by the first distance D1. It should be noted that each of the first patterned regions 200 is an N-sided polygon, and each of the second patterned regions 210 is an M-sided polygon. In the present embodiment, N and M are positive integers, and N is greater than M.

Specifically, as shown in FIG. 10, any two of the second patterned regions 210 adjacent to each other are spaced apart from each other by a second distance D2 that is greater than the first distance D1, and the second distance D2 is preferable less than an outer diameter D200 of any one of the first patterned regions 200.

Quasi-Soft Capture Device

The following description describes the quasi-soft capture device D of the present disclosure from different angles according to the above embodiments. The quasi-soft capture device D is also referred to as a capture device D. As shown in FIG. 11 and FIG. 12, the capture device D includes two catchers C and an adhesive layer 50 that is gaplessly connected to the two catchers C so as to jointly define a chamber 40. Moreover, the capture arms 20 of any one of the two catchers C face toward another one of the two catchers C, and the capture arms 20 of the two catchers C are arranged in the chambers 40.

Specifically, the capture device D has an opening 501 in spatial communication with the chamber 40 and an external space that is located outside of the capture device D, and the chamber 40 is configured to accommodate a specimen S through the opening 501. In the present embodiment, the opening 501 is formed in the adhesive layer 50, and the opening 501 is tapered along a direction from an outer surface of the adhesive layer 50 toward the chamber 40, so that any liquid (e.g., the specimen S) in the chamber 40 is unable to flow out of the chamber 40 through the opening 501, but the present disclosure is not limited thereto.

In addition, the two catchers C of the capture device D in the present embodiment are of the same structure, but the present disclosure is not limited thereto. For example, in other embodiments of the present disclosure, the two catchers C of the capture device D can have different structures so as to provide complementary capture capabilities.

Method For Using Quasi-Soft Capture Device

The following description describes the method for using the quasi-soft capture device D of the present disclosure from different angles according to the above embodiments. The method for using the quasi-soft capture device D is also referred to as a method for capturing at least one target biological particle that includes a preparing step, an injection step, a turning over step, and a sampling step. The following description describes each of the steps of the method, but each of the steps can be adjusted or changed according to design requirements and is not limited to the following description.

As shown in FIG. 11, the preparing step is implemented by providing the capture device D. It should be noted that the specific structure or the possible varied structure of the capture device D of the present embodiment is similar or identical to the capture device D that was disclosed in the above description.

As shown in FIG. 11 and FIG. 12, the injection step is implemented by injecting a specimen S into the chamber 40 through the opening 501 until the chamber 40 is fully filled with the specimen S. In other words, the method of the present embodiment does not use any fluid channel to capture the target biological particle T.

The turning over step is implemented by gradually turning over the capture device D to exchange the positions of the two catchers C after waiting for a predetermined period of time after the injection step is performed. Specifically, the predetermined period of time can be within a range of 5-15 minutes, and can also be adjusted or changed according to design requirements. In the present embodiment, the capture device D is fastened to a carrier (not shown), and is gradually overturned by using the carrier, but the present disclosure is not limited thereto. In addition, the exchange of position of the two catchers C means that the capture device D is overturned by 180 degrees, so that any of the two catchers C is moved to the position of another one of the two catchers C.

As shown in FIG. 12 and FIG. 13, the sampling step is implemented by removing a liquid of the specimen S from the chamber 40 and cutting the supporting segments 22 of each of the two catchers C in a mechanical manner so as to separate the free end portions 21 from the base 10 and to obtain the free end portions 21 of each of the two catchers C (and at least one captured target biological particle T).

Moreover, after the turning over step is performed, the sampling step is preferably implemented after the predetermined period of time, but the present disclosure is not limited thereto. The liquid is removed from the chamber 40 and the supporting segments 22 of each of the two catchers C are cut in the mechanical manner after destroying the adhesive layer 50 to separate the two catchers C from each other.

In conclusion, the quasi-soft catcher and the method of the present disclosure are provided to increase the success rate of capturing a single target biological particle and to separate each of the target biological particles from quasi-soft catcher intact by the technical solution of "the protruding structures extends from the board surface and regularly arranged, each of the protruding structures includes an outer portion configured to touch at least one target biological particle and an inner portion that is connected between the board surface and the outer portion, a structural strength of the inner portion of each of the protruding structures is less than that of the corresponding outer portion, and the board surface has an interspace region arranged outside of the protruding portions, and the interspace region occupies 20-80% of the board surface."

Specifically, the quasi-soft catcher of the present disclosure can be provided to ensure that the target biological particles have a very high capture rate while remaining intact. Moreover, the structural strength of the inner portion is less than that of the outer portion, so that the obtaining device can easily cut the inner portion to ensure that the target biological particles can be smoothly separated from the quasi-soft catcher without being punctured or scratched. Furthermore, the quasi-soft catcher of the present disclosure is suitable for high-throughput analysis, and can be used to capture the target biological particles from a limited amount of specimen, so that the target biological particles can be effectively removed from the quasi-soft catcher and the subsequent tests or analysis can be directly performed. Accordingly, it is not necessary to collect specimens again to separate the target biological particles, thereby achieving the effect of reducing an operation cost and time of detection.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A capture device for being applied to capture a target biological particle from a specimen, comprising:
   two catchers each including a base and a plurality of capture arms extending from the base and spaced apart from each other, wherein each of the capture arms has a free end portion configured to capture a target biological particle and a supporting segment connected between the free end portion and the base, and wherein the supporting segment of each of the capture arms is arranged in a projection space defined by orthogonally projecting the free end portion along a height direction onto the base; and
   an adhesive layer gaplessly connected to the two catchers so as to jointly define a chamber, wherein the capture arms of any one of the two catchers face toward another one of the two catchers, and the capture arms of the two catchers are arranged in the chambers,
   wherein the capture device has an opening that is spatially communicated between the chamber and an external space that is located outside of the capture device, and the chamber is configured to accommodate a specimen through the opening, and
   wherein when the specimen is accommodated in the chamber, and the target biological particle is captured by two of the capture arms that are arranged adjacent to each other, the free end portion of any one of the two of the capture arms is attached with and carries the target biological particle so as to bend the corresponding supporting segment to have an elastic force, and a part of the target biological particle is trapped by the supporting segments of the two of the capture arms and is held by the elastic force.

2. The capture device according to claim 1, wherein the opening is formed in the adhesive layer, and wherein the opening is tapered along a direction from an outer surface of the adhesive layer toward the chamber, so that any liquid in the chamber is unable to flow out of the chamber through the opening.

3. The capture device according to claim 1, wherein in each of the capture arms, the free end portion has an end surface arranged away from the supporting segment and at least one guiding surface connected to the end surface, wherein the at least one guiding surface of any one of the capture arms is configured to provide a lateral force to the corresponding supporting segment so as to tend to maintain the corresponding supporting segment in a curved shape when being attached with the target biological particle, and wherein the lateral force is non-parallel to the height direction.

4. The capture device according to claim 1, wherein in each of the capture arms, the free end portion has an end surface arranged away from the supporting segment and at least one guiding surface connected to the end surface, and wherein the guiding surfaces of at least two of the capture arms arranged adjacent to each other jointly define a notch that is configured to guide and trap the part of the target biological particle.

5. The capture device according to claim 1, wherein in each of the capture arms, an outer surface of the supporting segment is an etched lateral surface, so that the supporting segment is cuttable along a direction perpendicular to the height direction in a mechanical manner.

6. The capture device according to claim 1, wherein in each of the two catchers, the capture arms are distributed as a plurality of first patterned regions, any two of the first patterned regions adjacent to each other are spaced apart from each other by a first distance, any two of the capture arms of each of the first patterned regions adjacent to each other have an internal interval there-between, and the first distance is greater than the internal interval.

7. A method for capturing at least one target biological particle, comprising:
   a preparing step implemented by providing the capture device according to claim 1;
   an injection step implemented by injecting a specimen into the chamber through the opening until the chamber is fully filled with the specimen;
   a turning over step implemented, after the injection step, by gradually turning over the capture device to exchange positions of the two catchers after waiting for a predetermined period of time; and
   a sampling step implemented by removing a liquid of the specimen from the chamber and cutting the supporting segments of each of the two catchers in a mechanical manner so as to separate the free end portions from the base and to obtain the free end portions of each of the two catchers.

8. The method according to claim 7, wherein in the sampling step, the liquid is removed from the chamber and the supporting segments of each of the two catchers are cut in the mechanical manner after destroying the adhesive layer to separate the two catchers from each other.

9. The method according to claim 7, wherein in the turning over step, the predetermined period of time is within a range of 5-15 minutes, and wherein the sampling step is implemented, after the turning over step, by waiting for the predetermined period of time.

10. A catcher for being applied to capture at least one target biological particle from a specimen, comprising:
   a base; and
   a plurality of capture arms extending from the base and spaced apart from each other, wherein each of the capture arms has a free end portion configured to capture a target biological particle and a supporting segment connected between the free end portion and the base, and wherein the supporting segment of each of the capture arms is arranged in a projection space defined by orthogonally projecting the free end portion along a height direction onto the base,
   wherein when the target biological particle is captured by two of the capture arms that are arranged adjacent to each other, the free end portion of any one of the two of the capture arms is attached with and carries the target biological particle so as to bend the corresponding supporting segment to have an elastic force, and a part of the target biological particle is trapped by the supporting segments of the two of the capture arms and is held by the elastic force.

11. The catcher according to claim 10, wherein in each of the capture arms, the free end portion has an end surface arranged away from the supporting segment and at least one guiding surface connected to the end surface, wherein the at least one guiding surface of any one of the capture arms is configured to provide a lateral force to the corresponding supporting segment so as to tend to maintain the corresponding supporting segment in a curved shape when being attached with the target biological particle, and wherein the lateral force is non-parallel to the height direction.

12. The catcher according to claim 10, wherein in each of the capture arms, the supporting segment includes a plurality of elongated parts connected to each other, and each of the elongated arms has two opposite ends respectively connected to the base and the free end portion, and wherein each of the supporting segments is bendable with respect to the height direction by a swing angle that is less than or equal to 5 degrees.

13. The catcher according to claim 10, wherein the capture arms are distributed to form a plurality of first patterned regions, any two of the first patterned regions adjacent to each other are spaced apart from each other by a first distance, any two of the capture arms of each of the first patterned regions adjacent to each other have an internal interval there-between, and the first distance is greater than the internal interval.

14. The catcher according to claim 10, wherein the supporting segment of any one of the capture arms has a maximum width greater than the internal interval, and the free end portion of any one of the capture arms has a maximum width greater than the internal interval.

15. The catcher according to claim 13, wherein the capture arms are further distributed to form a second patterned region arranged between any two of the first patterned regions that are spaced apart from each other by a distance more than two times of the first distance, and wherein each of the second patterned regions and any one of the first patterned regions adjacent thereto are spaced apart from each other by the first distance, and any two of the capture arms adjacent to each other and belonging to any one of the second patterned regions have the internal interval there-between.

16. The catcher according to claim 13, wherein the capture arms are further distributed to form a plurality of second patterned regions, wherein each of the second patterned regions is surrounded by at least three of the first patterned regions, and is spaced apart from any one of the first patterned regions adjacent thereto by the first distance, and wherein any two of the capture arms adjacent to each other and belonging to any one of the second patterned regions have the internal interval there-between.

17. The catcher according to claim 16, wherein any two of the second patterned regions adjacent to each other are spaced apart from each other by a second distance greater than the first distance, and wherein the second distance is less than an outer diameter of any one of the first patterned regions.

18. The catcher according to claim 16, wherein each of the first patterned regions is an N-sided polygon, and each of the second patterned regions is an M-sided polygon, and wherein N and M are positive integers, and N is greater than M.

19. The catcher according to claim 10, wherein the capture arms are in a matrix arrangement, and any two of the capture arms adjacent to each other have an internal interval there-between.

20. The catcher according to claim 10, wherein in each of the capture arms, an outer surface of the supporting segment is an etched lateral surface, so that the supporting segment is cuttable along a direction perpendicular to the height direction in a mechanical manner.

* * * * *